United States Patent
Anderson et al.

(10) Patent No.: US 12,324,825 B2
(45) Date of Patent: Jun. 10, 2025

(54) SYSTEMS AND METHODS OF TREATING PROSTATE CANCER

(71) Applicants: Dean Gregory Anderson, Vernal, UT (US); Dean Robert Gary Anderson, Orem, UT (US)

(72) Inventors: Dean Gregory Anderson, Vernal, UT (US); Dean Robert Gary Anderson, Orem, UT (US)

(*) Notice: Subject to any disclaimer, the term of this patent is extended or adjusted under 35 U.S.C. 154(b) by 0 days.

(21) Appl. No.: 17/964,023

(22) Filed: Oct. 11, 2022

(65) Prior Publication Data

US 2023/0113951 A1  Apr. 13, 2023

Related U.S. Application Data

(60) Provisional application No. 63/253,701, filed on Oct. 8, 2021.

(51) Int. Cl.
*A61K 38/00* (2006.01)
*A61K 38/09* (2006.01)

(52) U.S. Cl.
CPC .................................. *A61K 38/09* (2013.01)

(58) Field of Classification Search
CPC ...................................................... A61K 38/09
See application file for complete search history.

(56) References Cited

FOREIGN PATENT DOCUMENTS

WO    WO-2018080933 A1 *    5/2018    ........... A61K 31/122

OTHER PUBLICATIONS

Michael T. Schweizer, et al., Effect of bipolar androgen therapy for asymptomatic men with castration-resistant prostate cancer: Result from a pilot clinical study, Science Translational Medicine, American Association for the Advancement of Science., Jan. 7, 2015, vol. 7, Issue 269.

Michael T. Schweizer, et al., Bipolar Androgen Therapy for Men With Androgen Ablation Naive Prostate Cancer: Results From the Phase II Batman Study, The Prostate, Wiley Periodicals, Inc., Sep. 15, 2016, vol. 76, Issue 13.

Benjamin A. Teply, et al., Bipolar androgen therapy in men with metastatic castration-resistant prostate cancer after progression on enzalutamide: an open-label, phase 2, multicohort study, Lancet Oncology, Mar. 29, 2018, vol. 19, Issue 1.

Samuel R. Denmeade, et al., Transformer: A Randomized Phase II Study Comparing Bipolar Androgen Therapy Versus Enzalutamide in Asymptomatic Men With Castration-Resistant metastatic Prostate Cancer, Journal of Clinical Oncology, Feb. 22, 2021, vol. 39, Issue 12.

David Feltquate, et al., Rapid Androgen Cycling as Treatment for Patients with Prostate Cancer, Clinical Cancer Research, Dec. 15, 2006, vol. 12, Issue 24.

Russell Szmulewitz, et al, A Randomized Phase 1 Study of Testosterone Replacement for Patients with low-Risk Castration-Resistant Prostate Cancer, European Urology, European Association of Urology, Elsevier, Feb. 27, 2009, vol. 56, Issue 1.

Michael J. Morris, et al., Phase 1 Trial of High-Dose Exogenous Testosterone in Patients with Castration-Resistant Metastatic Prostate Cancer, European Urology, European Association of Urology, Aug. 2009, vol. 56, Issue 2.

Tao Xie, et al., The role of androgen therapy in prostate cancer: from testosterone replacement therapy to bipolar androgen therapy, Drug Discovery Today, May 5, 2021, vol. 26, No. 5.

* cited by examiner

Primary Examiner — Jeanette M Lieb
(74) Attorney, Agent, or Firm — Daniel J. Anderson

(57) ABSTRACT

In one embodiment, a prostate cancer patient can be treated with several novel approaches to bipolar androgen therapy. According to various embodiments, a combination of external beam radiation with bipolar androgen therapy can be used. According to various embodiments, one or more of intravenous injection, transdermal application and/or buccal administration of testosterone can be used to significantly decrease the length of time spent tapering between supraphysiologic and castrate levels of testosterone.

20 Claims, 2 Drawing Sheets

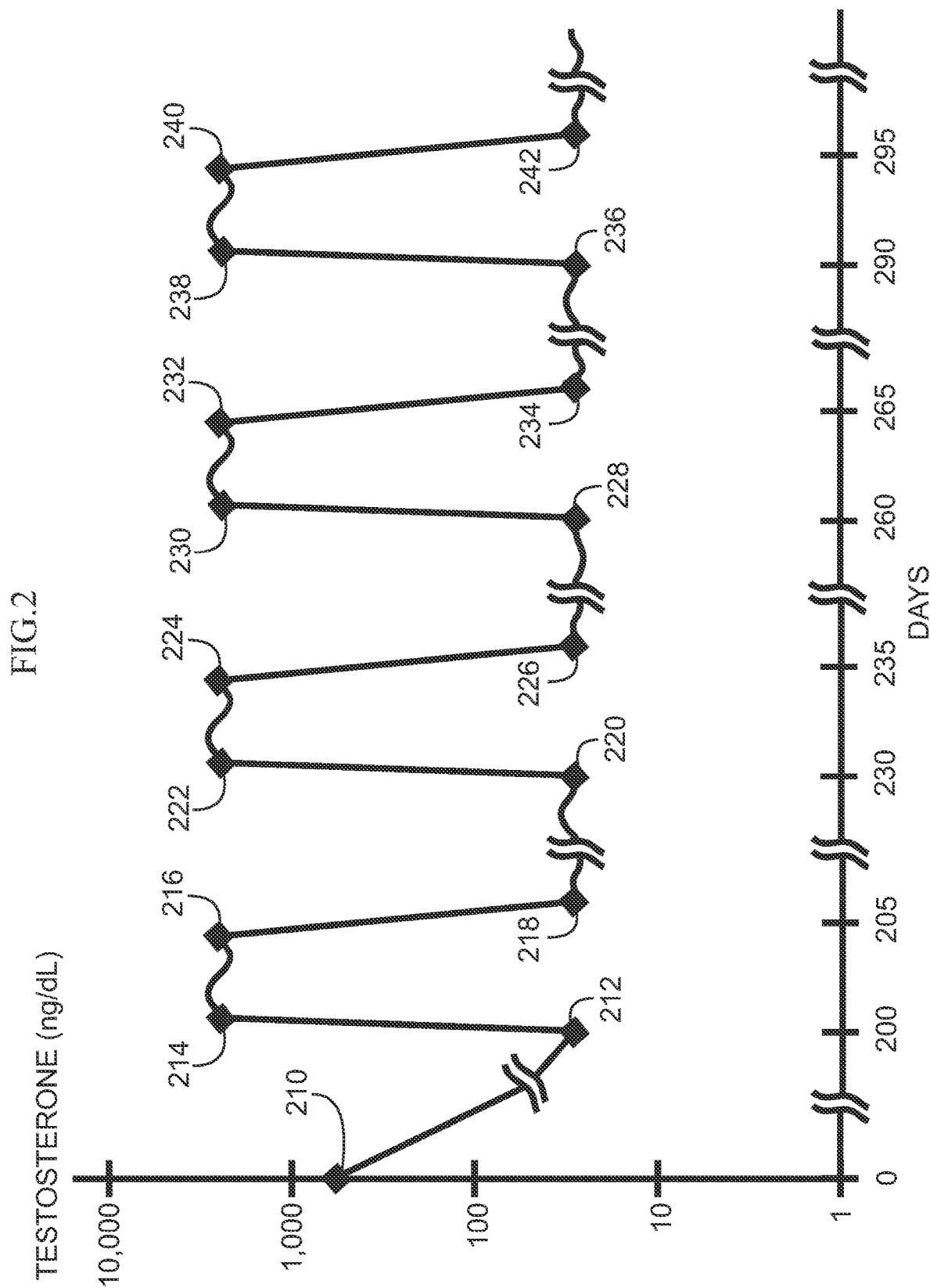

SYSTEMS AND METHODS OF TREATING PROSTATE CANCER

CROSS-REFERENCE TO RELATED APPLICATIONS

The application claims priority to U.S. Provisional Application No. 63/253,701 filed on Oct. 8, 2021, the content of which is hereby incorporated by reference.

BACKGROUND

The present invention relates, in general, to methods for treating prostate cancer, and more particularly to methods of administering and controlling testosterone for bipolar androgen therapy, and the combination of bipolar androgen therapy with other therapies such as external beam radiation or brachytherapy.

Early-stage prostate cancer cells require androgen hormones (such as testosterone) to grow. Androgen deprivation therapy is a conventional therapy in which medications, surgery, and/or procedures are used to reduce androgen hormones in the patient and slow the growth of the prostate cancer cells. Even in low androgen conditions, prostate cancer in advanced stages may become resistant to castration and continue to grow. Such cancer is known as castration-resistant prostate cancer ("CRPC").

One approach to treating castration-resistant prostate cancer includes bipolar androgen therapy wherein intramuscular injection of testosterone is used to achieve supraphysiologic levels (>1,000 ng/dL) of serum testosterone. The supraphysiologic levels of androgen overloads the androgen receptors of the CRPC cells and disrupts their ability to divide/grow.

Intramuscular injection can produce supraphysiologic levels of testosterone within 2 days of injection. However, two weeks after the injection, the patient may still have a high normal level of testosterone and four weeks after injection the level can still be above castrate levels (>50 ng/dL). As a result, there is a long transition time from supraphysiologic levels to castrate levels of serum testosterone. During this transition, the prostate cancer cells may experience weeks of normal physiologic levels of testosterone which may promote the growth of prostate cancer.

There remains a need for an improved bipolar androgen therapy which is optimized for the treatment of prostate cancer. There remains a need for an improved bipolar androgen therapy that reduces the duration of normal physiologic levels of testosterone in a patient undergoing bipolar androgen therapy. There remains a need for an improved administration of testosterone during bipolar androgen therapy that would further enhance the efficacy of the treatment. There remains a need for the combination of bipolar androgen therapy with other modalities to improve the overall efficacy of both treatments.

BRIEF DESCRIPTION OF THE DRAWINGS

FIG. 2 illustrates a treatment schedule and associated testosterone levels in a patient treated with bipolar androgen therapy according to various embodiments.

Figure 1:
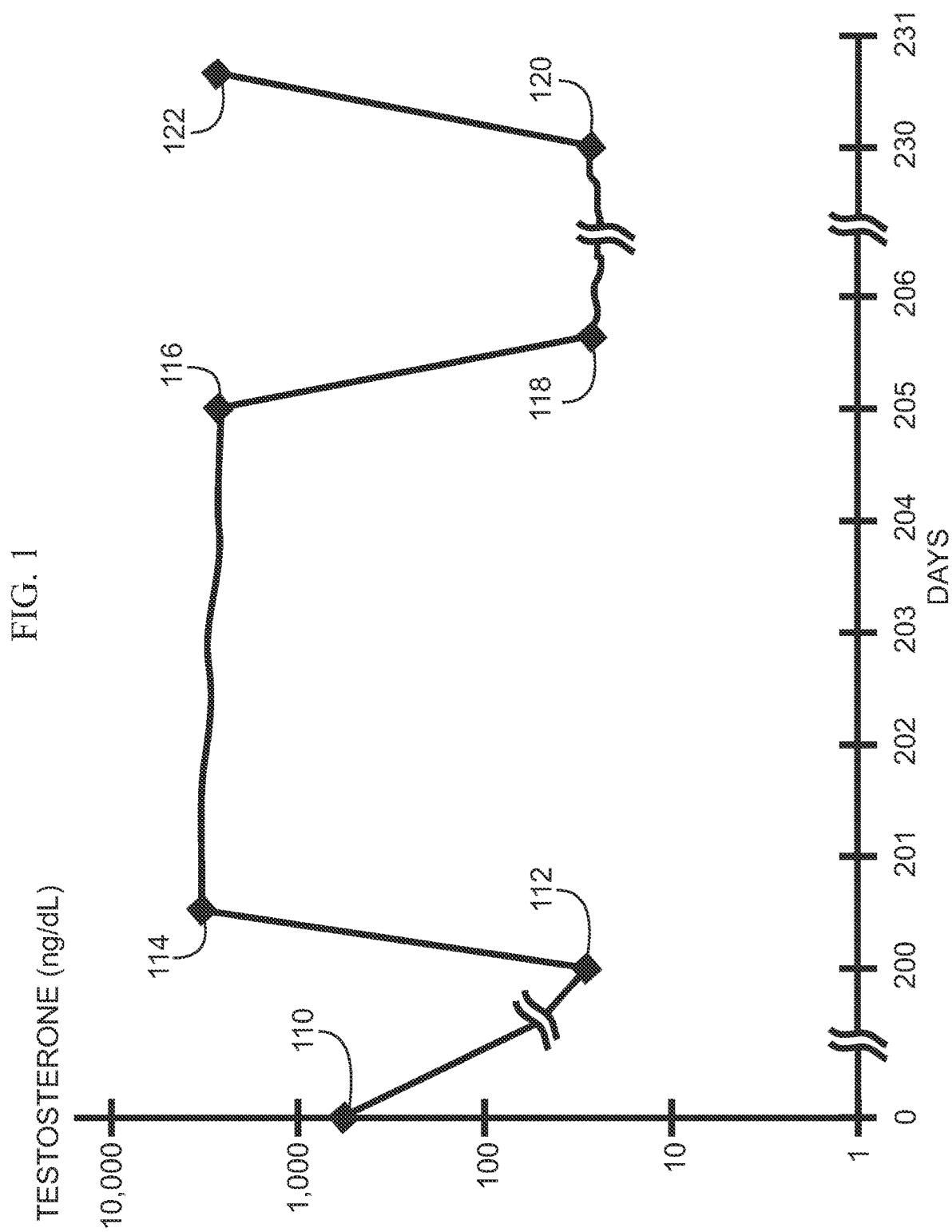
FIG. 1 illustrates a treatment schedule and associated testosterone levels in a patient treated with bipolar androgen therapy according to various embodiments.

The drawings and detailed description are provided in order to enable a person of ordinary skill in the applicable art to make and use the invention. The timing, duration, testosterone levels, examples, etc., and the written descriptions are illustrative and not intended to be limiting of the disclosure. Descriptions and details of well-known steps and elements are omitted for simplicity of the description. For example, dosing requirements, frequency of application, and application directions, of exogenous androgen mechanisms required to achieve a desired blood testosterone level in a particular patient can be calculated and determined according to the manufacturer's information disclosures. For example, a buccal androgen administration may require mucoadhesive devices, each containing 30 mg of testosterone. Depending on the patient's age, weight and individual metabolism of testosterone, one or more mucoadhesive devices may need to be applied to the patient's upper gum near the labial frenulum. The mucoadhesive device(s) may provide a controlled and sustained release of testosterone through the buccal mucosa as the mucoadhesive device hydrates. Removal and application of new mucoadhesive device(s) may occur twice daily.

As used herein, the term and/or includes any and all combinations of one or more of the associated listed items. In addition, the terminology used herein is for the purpose of describing particular embodiments only and is not intended to be limiting of the disclosure. As used herein, the singular forms are intended to include the plural forms as well, unless the context clearly indicates otherwise. It will be further understood that the terms comprise, comprises, comprising, include, includes, and/or including, when used in this specification and claims, are intended to specify a non-exclusive inclusion of stated features, drugs, compounds, rounds, periods, levels, ranges, and/or mechanisms, and do not preclude the presence or addition of one or more other features, drugs, compounds, rounds, periods, levels, ranges, and/or mechanisms thereof.

It will be understood that, although the terms first, second, etc. may be used herein to describe various features, drugs, compounds, rounds, periods, levels, ranges, and/or mechanisms, such features, drugs, compounds, rounds, periods, levels, ranges, and/or mechanisms should not be limited by these terms. These terms are only used to distinguish one feature, drug, compound, round, period, level, range, and/or mechanism from another.

Reference to "one embodiment" or "an embodiment" means that a particular feature or characteristic described in connection with the embodiment is included in at least one embodiment of the present disclosure. Thus, appearances of the phrases "in one embodiment" or "in an embodiment" in various places throughout this specification are not necessarily all referring to the same embodiment, but in some cases it may.

The use of words about, approximately or substantially means a value of an element is expected to be close to a stated value or position. However, as is well known in the art there are always minor variances preventing values or positions from being exactly stated. It is further understood that the embodiments illustrated and described hereinafter suitably may have embodiments and/or may be practiced in the absence of any step/element that is not specifically disclosed herein. Furthermore, it is understood that in some cases the embodiments illustrated and described hereinafter suitably may have embodiments and/or may be practiced with one or more of the illustrated or described steps omitted.

The inventors are fully informed of the standards and application of the special provisions of 35 U.S.C. § 112(f). Thus, the use of the words "function," "mechanism" "means" or "step" in the Detailed Description of the Invention or claims is not intended to somehow indicate a desire to invoke the special provisions of 35 U.S.C. § 112(f), to define the invention. To the contrary, if the provisions of 35 U.S.C. § 112(f) are sought to be invoked to define the inventions, the claims will specifically and expressly state the exact phrases "means for" or "step for" and the specific function (e.g., "means for filtering"), without also reciting in such phrases any structure, material or act in support of the function. Thus, even when the claims recite a "means for . . . " or "step for . . . " if the claims also recite any structure, material, or acts in support of that means or step, or that perform the recited function, then it is the clear intention of the inventor not to invoke the provisions of 35 U.S.C. § 112(f). Moreover, even if the provisions of 35 U.S.C. § 112(f) are invoked to define the claimed inventions, it is intended that the inventions not be limited only to the specific structure, material or acts that are described in the illustrated embodiments, but in addition, include any and all structures, materials, or acts that perform the claimed function as described in alternative embodiments or forms of the invention, or that are well known present or later-developed, equivalent pharmaceuticals, material, or acts for performing the claimed function.

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known methods and devices are shown or discussed more generally in order to avoid obscuring the invention. In many cases, a description of the patient testosterone levels over time is sufficient to enable one to implement the various forms of the invention. Thus, the full scope of the invention is not limited to the examples that are described below.

DETAILED DESCRIPTION OF THE DRAWINGS

According to various embodiments, intravenous injection of testosterone can be used with bipolar androgen therapy instead of intramuscular injection to achieve supraphysiologic levels of testosterone. The use of intravenous injection of testosterone allows for very precise control of dosing and control over the level of blood testosterone of the patient. It is noted, however, that such an application would require intravenous access and may require a pump.

According to various embodiments, an above-normal dosage of a transdermal administration of testosterone can be used to produce supraphysiologic levels of testosterone in a patient treated with bipolar androgen therapy.

According to various embodiments, an above-normal dosage of a transdermal administration of testosterone can be used to produce supraphysiologic levels of testosterone in a patient within 1-4 days according to the embodiments described herein.

When transdermal administration of testosterone is discontinued after supraphysiologic levels are achieved and maintained for a desired period of time, the serum concentration may return to pretreatment levels within 3 to 8 days according to the embodiments described herein. This is a vast improvement over the conventional use of intramuscular injection to achieve supraphysiologic levels of testosterone according to conventional methods.

According to various embodiments, discontinuing a transdermal administration can comprise removing the transdermal application of an androgen from the subject by cleaning the subject's skin.

According to various embodiments, an above-normal dosage of a buccal administration of testosterone can be used to produce supraphysiologic levels of testosterone in a patient treated with bipolar androgen therapy.

According to various embodiments, an above-normal dosage of a buccal administration of testosterone can be used to produce supraphysiologic levels of testosterone in a patient within 24 hours according to the embodiments described herein.

When buccal administration of testosterone is discontinued after supraphysiologic levels are achieved and maintained for a desired period of time, the serum concentration may return to pretreatment levels within 24 hours according to the embodiments described herein. This is a vast improvement over the conventional use of intramuscular injection to achieve supraphysiologic levels of testosterone according to conventional methods.

According to various embodiments, discontinuing a buccal administration can comprise removing the mechanism comprising the buccal administration of androgen from the mouth of the subject.

According to various embodiments, one or more of intravenous injection, transdermal application, or buccal administration of testosterone can be used at increased doses to produce supraphysiologic levels of testosterone for an improved bipolar androgen therapy. According to the various embodiments described herein, supraphysiologic levels of testosterone can be considered to comprise levels of testosterone above 1,000 ng/dL. For example, about 1,500 ng/dL, or about 3,000 ng/dL, or even greater than 3,500 ng/dL, are all example embodiments of supraphysiologic levels of testosterone according to various embodiments.

According to various embodiments, the duration of the administration of exogenous testosterone can continue for between 2 to 10 days, after which the administration of testosterone can be discontinued.

According to various embodiments, a new round of administration of testosterone can be applied within 5 to 31 days after the completion of the previous administration of testosterone.

According to various embodiments, the use of intravenous injection, transdermal application, or buccal administration of testosterone can provide the advantage of a significantly shortened lengths of time in which the prostate cancer experiences normal physiologic levels of testosterone after the termination of the administration of testosterone when compared with the use of intramuscular dosing.

FIG. 1 illustrates a treatment schedule and associated testosterone levels in a patient over time treated with bipolar androgen therapy according to various embodiments described herein.

The y-axis of FIG. 1 represents the testosterone level of a patient according to an embodiment as measured in nanograms per deciliter. The y-axis is shown in a logarithmic scale. The x-axis of FIG. 1 represents time as measured in days. For simplicity certain time periods, such as the time period between 0 and 200 days are abbreviated.

A first testosterone level 110 of the prostate cancer patient is shown on day 0 at around 300-1000 ng/dL. This level represents the patient's normal testosterone level. At this point in time the patient begins a treatment to suppress the patient's natural production of androgen. For example, the patient may undergo a surgery or other procedure designed to suppress the patient's natural production of androgen. Alternatively, the patient can begin an administration of one or more androgen deprivation pharmaceutical drugs. The androgen deprivation pharmaceutical drug can comprise Leuprolide, Goserelin, Triptorelin, Buserelin, Histrelin, or another pharmaceutical drug known for use in androgen depravation therapy.

The androgen deprivation pharmaceutical drug can suppress the patient's natural production of androgen. According to an embodiment, the androgen deprivation pharmaceutical drug is administered in order to suppress the patient's natural production of androgen below castrate levels. The androgen deprivation pharmaceutical drug can be administered to the patient according to known techniques over a first period of time. According to FIG. 1 the androgen depravation pharmaceutical drug is administered in order to reduce the patient's testosterone below castrate levels (around 50 ng/dL or below). According to FIG. 1, the patient achieved a castrate level of testosterone around day 40. According to various embodiments, the patient will continue the administration of androgen deprivation pharmaceutical drug for a first period of time. According to one embodiment, the first period of time is greater than 1 month. According to another embodiment, the first period of time is greater than 3 months. According to another embodiment, the first period of time is greater than 6 months. According to another embodiment, the first period of time is greater than 12 months. According to yet another embodiment, the first period of time is greater than 24 months.

According to FIG. 1, the patient reaches a second testosterone level 112 of about 10-50 ng/dL on day 200. At this time, the patient has been below castrate levels of testosterone for 160 days. At this time the patient can begin an administration of exogenous androgen via a first mechanism. The administration of the exogenous androgen marks the beginning of the second period of time. According to one embodiment, the first mechanism can include an intravenous injection of an androgen. According to another embodiment, the first mechanism can comprise a buccal administration of androgen. According to another embodiment, the first mechanism can comprise a transdermal administration of androgen. The administration of exogenous androgen is designed to achieve and maintain supraphysiologic levels (greater than 1,000 ng/dL) of serum testosterone in the patient.

The supraphysiologic level of testosterone is achieved and maintained for the remainder of the second period of time. According to one embodiment the second period of time can be between 1 and 7 days. According to one embodiment, the second period of time can be 5 days. According to various embodiments, the second period of time overlaps the first period of time and runs contemporaneously with the first period of time.

The third blood testosterone level 116 marks the end of the second period of time and the beginning of the third period of time. At the end of the second period of time, and the beginning of the third period of time, the administration of exogenous androgen is reduced or discontinued. After the administration of exogenous androgen is reduced or discontinued (e.g., by removing the androgen from the intravenous delivery mechanism, removing the buccal mechanism, or washing the transdermal mechanism from the patient's skin) the patient's blood testosterone level can decline back to previous castrate levels because the patient may still be administering an androgen deprivation pharmaceutical drug.

According to a buccal bipolar androgen therapy treatment embodiment, the time between point 112 and point 114 required to achieve a supraphysiologic level of blood testosterone within the patient can be between 1-4 hours or under less than 24 hours.

According to a buccal bipolar androgen therapy treatment embodiment, the time between point 116 and point 118 required to achieve a blood testosterone level below castrate levels can be within 3-9 hours or less than 24 hours.

According to a transdermal bipolar androgen therapy treatment embodiment, the time between point 112 and point 114 required to achieve a supraphysiologic level of blood testosterone within the patient can be between 1-4 days.

According to a transdermal bipolar androgen therapy treatment embodiment, the time between point 116 and point 118 required to achieve a blood testosterone level below castrate levels can be within 3-8 days.

Referring to FIG. 1, once the patient has again achieved castrate level of blood testosterone 118, the patient may continue to administer an androgen deprivation pharmaceutical drug in order to maintain a blood testosterone level at or below a castrate level for the remainder of the third period of time. According to various embodiments the third period of time can be between 5 and 31 days. According to one embodiment the third period of time is 25 days. According to various embodiments, the third period of time overlaps the first period of time and runs contemporaneously with the first period of time.

At the end of the third period of time, the patient can begin a second round of administering exogenous androgen via a second mechanism. The second-round administration of exogenous androgen marks the beginning of a fourth period of time. The second round of administration of exogenous androgen is designed to achieve and maintain at least the level of blood testosterone 122. According to various embodiments, the level of blood testosterone 122 is greater than 1,000 ng/dL. According to various embodiments, the level of blood testosterone 122 is around the same as the level of blood testosterone 114 or 116. During the second round, the second mechanism of administering exogenous androgen can be the same as the first round or a different mechanism.

The supraphysiologic level of testosterone 122 is achieved and maintained for the remainder of the fourth period of time. According to one embodiment the fourth period of time can be between 1 and 7 days. According to one embodiment, the fourth period of time can be 5 days. According to various embodiments, the fourth period of time overlaps the first period of time and runs contemporaneously with the first period of time.

At the end of the fourth period of time, and the beginning of the fifth period of time, the administration of exogenous androgen can be reduced or discontinued. After the administration of exogenous androgen is reduced or discontinued (e.g., by removing the androgen from the intravenous delivery mechanism, removing the buccal mechanism, or washing the transdermal mechanism from the patient's skin) the patient's blood testosterone level can decline back to previous castrate levels because the patient may still be administering an androgen deprivation pharmaceutical drug.

Additional rounds of treatment as described above can be administered in succession. For example, three successive rounds of achieving supraphysiologic blood testosterone levels, each followed by a rapid decline to castrate levels of blood testosterone can be administered followed by a break period during which no additional rounds of supraphysiologic blood testosterone levels are achieved. The break period may last for anywhere between a month and a year, after which successive rounds of achieving supraphysiologic blood testosterone levels, each followed by a rapid decline to castrate levels of blood testosterone can be administered. According to some embodiments, during the break period, the patient may continue to administer androgen deprivation pharmaceutical drugs. According to another embodiment, during the break period the patient may discontinue administration of all androgen deprivation and exogenous androgen drugs.

FIG. 2 illustrates a treatment schedule and associated testosterone levels in a patient over time treated with bipolar androgen therapy according to various embodiments described herein. FIG. 2 illustrates four successive rounds of achieving supraphysiologic blood testosterone levels, each followed by a rapid decline to castrate levels of blood testosterone. The four successive rounds shown in FIG. 2 may be followed by a break period, or alternatively additional successive rounds may be administered.

According to various embodiments, the mechanism of bipolar androgen therapy-induced inhibition of prostate cancer cell growth and death is determined to be multimodal.

One of these mechanisms involves TOP2β mediated DNA double stranded breaks in the regulatory regions of androgen receptor target genes.

According to various embodiments, this is determined to result in apoptosis of the prostate cancer cell. External beam radiation therapy likewise works by damaging the DNA of prostate cancer cells, again resulting in cell death.

According to various embodiments, brachytherapy and/or external beam radiation therapy can be combined with the above-described bipolar androgen therapy to achieve improvements in each treatment. For example, a patient may receive external beam radiation therapy during the initial round or rounds of the above-described bipolar androgen therapy. The combination of the two therapies can result in improved efficacy of the patient's overall treatment.

According to various embodiments, the above-described bipolar androgen therapy can be administered to patients at any stage of prostate cancer, including early stages when the prostate cancer cells are still sensitive to castration and late stages when the prostate cancer cells may be castration resistant.

In reference to all of the foregoing disclosure, the above-described embodiments enable systems, methods, and therapies comprising improvements, benefits, and solutions to problems and issues affecting conventional bipolar androgen therapy.

The hereinafter expressed claims are hereby expressly incorporated into this Detailed Description of the Drawings, with each claim standing on its own as a separate embodiment of the invention.

What is claimed is:

1. A method of treating prostate cancer in a patient comprising:
    suppressing the patient's natural production of androgen with a first pharmaceutical drug over a first period of time, wherein suppressing the patient's natural production of androgen comprises decreasing the patient's blood testosterone level below 50 ng/dL during at least a first portion of the first period of time;
    administering exogenous androgen to the patient via a first mechanism wherein administering exogenous androgen comprises increasing the patient's blood testosterone level above 1,000 ng/dL;
    maintaining the patient's blood testosterone level above 1,000 ng/dl for a second period of time; and
    discontinuing the administration of exogenous androgen for a third period of time commencing after the second period of time, wherein discontinuing the administration of exogenous androgen results in the patient's blood testosterone level dropping from a value above 1,000 ng/dL to a value below 50 ng/dl within less than 5 days.

2. The method of claim 1, wherein the first mechanism comprises a buccal administration of exogenous androgen.

3. The method of claim 1, wherein the first mechanism comprises a transdermal administration of exogenous androgen.

4. The method of claim 1, wherein the first mechanism comprises an intravenous administration of exogenous androgen.

5. The method of claim 1, wherein the pharmaceutical drug comprises Leuprolide.

6. The method of claim 1, wherein the pharmaceutical drug comprises Goserelin.

7. The method of claim 1, wherein the pharmaceutical drug comprises Triptorelin.

8. The method of claim 1, wherein the first period of time is greater than 3 months.

9. The method of claim 1, wherein the first period of time is greater than 12 months.

10. The method of claim 1, wherein the second period of time is between 1 to 7 days.

11. The method of claim 1, wherein at least a portion of the first period of time and a portion of the second period of time are contemporaneous.

12. The method of claim 1, wherein at least a portion of the first period of time and a portion of the third period of time are contemporaneous.

13. The method of claim 1, wherein the third period of time is between 5 to 31 days.

14. The method of claim 1, wherein the third period of time is about 24 days.

15. The method of claim 1, further comprising:
    administering a second round of exogenous androgen to the subject via a second mechanism, wherein the second round of exogenous androgen increases the patient's blood testosterone level above 1,000 ng./dL;
    maintaining the subject's blood testosterone level above 1,000 ng/dl during a fourth period of time; and
    discontinuing the administration of the second round of exogenous androgen during at least a fifth period of time commencing after the end of the fourth period of time.

16. The method of claim 15, wherein the first and second mechanism comprise the same mechanism.

17. The method of claim 15, wherein the fourth period of time is between 1 to 7 days.

18. The method of claim 15, wherein at least a portion of the first period of time and at least a portion of the fifth period of time overlap.

19. The method of claim 15, wherein the fifth period of time is between 5 and 31 days.

20. A method of treating prostate cancer in a patient comprising:
    suppressing the patient's natural production of androgen with a first pharmaceutical drug over a first period of time, wherein suppressing the patient's natural production of androgen comprises decreasing the patient's blood testosterone level below 50 ng/dL during at least a first portion of the first period of time;
    administering exogenous androgen to the patient via a buccal administration wherein administering exogenous androgen comprises increasing the patient's blood testosterone level above 1,500 ng/dL;
    maintaining the patient's blood testosterone level above 1,500 ng/dl for a second period of time; and discontinuing the administration of exogenous androgen for a third period of time commencing after the second period of time, wherein discontinuing the administration of exogenous androgen results in the patient's blood testosterone level dropping from a value above 1,500 ng/dl to a value below 50 ng/dl within less than 1 day.

* * * * *